United States Patent
Young

(10) Patent No.: US 12,226,242 B2
(45) Date of Patent: *Feb. 18, 2025

(54) SAFETY APPARATUS

(71) Applicants: VENNER MEDICAL TECHNOLOGIES SA, Jersey (GB); Maryanne Mariyaselvam, King's Lynn (GB); Peter Jeffrey Young, King's Lynn (GB)

(72) Inventor: Peter Jeffrey Young, King's Lynn (GB)

(73) Assignees: VENNER MEDICAL TECHNOLOGIES SA, Jersey (GB); Maryanne Mariyaselvam, King's Lynn (GB); Peter Jeffrey Young, King's Lynn (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/570,242

(22) Filed: Jan. 6, 2022

(65) Prior Publication Data

US 2022/0142726 A1 May 12, 2022

Related U.S. Application Data

(63) Continuation of application No. 15/752,874, filed as application No. PCT/GB2016/052536 on Aug. 16, 2016, now Pat. No. 11,246,676.

(30) Foreign Application Priority Data

Aug. 16, 2015 (GB) .................. 1514560
Dec. 15, 2015 (GB) .................. 1522150
Dec. 16, 2015 (GB) .................. 1522226

(51) Int. Cl.
*A61B 50/30* (2016.01)
*A61B 50/00* (2016.01)

(52) U.S. Cl.
CPC ........ *A61B 50/30* (2016.02); *A61B 2050/005* (2016.02); *A61B 2050/0056* (2016.02);
(Continued)

(58) Field of Classification Search
CPC ............ A61B 50/30; A61B 2050/3015; A61B 2050/311; B65D 50/067; B65D 2543/00989
See application file for complete search history.

(56) References Cited

U.S. PATENT DOCUMENTS

| 4,562,047 A | 12/1985 | Sestak et al. |
| 6,658,903 B1 | 12/2003 | McShane et al. |

(Continued)

FOREIGN PATENT DOCUMENTS

| CN | 202207318 U | 5/2012 |
| CN | 104078074 A | 10/2014 |

(Continued)

OTHER PUBLICATIONS

Linda T. Kohn, et al., "To Err is Human: Building a Safer Health System", Institute of Medicine, 1999, 34 pages, National Academy Press, Washington.

(Continued)

*Primary Examiner* — Javier A Pagan
(74) *Attorney, Agent, or Firm* — BakerHostetler

(57) ABSTRACT

A safety apparatus is provided for use in a procedure comprising at least first and second devices, wherein the first device and second device are for use in a medical procedure. The apparatus includes a disabling mechanism that is adapted to releasably retain and thereby prevent use of the said second device until release by a release procedure using the first device. A method is provided of carrying out a procedure comprising the steps of using the first device, (Continued)

applying the first device to a disabling mechanism to release the second device, and using the second device.

39 Claims, 6 Drawing Sheets

(52) U.S. Cl.
CPC ............... *A61B 2050/0067* (2016.02); *A61B 2050/0078* (2016.02); *A61B 2050/0079* (2016.02)

(56) References Cited

U.S. PATENT DOCUMENTS

| | | | |
|---|---|---|---|
| 11,246,676 B2 * | 2/2022 | Young | .................... A61B 50/30 |
| 2010/0059560 A1 | 3/2010 | Lanum | |
| 2010/0072270 A1 | 3/2010 | Creaven et al. | |
| 2012/0275957 A1 * | 11/2012 | Creaven | ........... G01N 33/48778 422/68.1 |
| 2013/0081966 A1 | 4/2013 | DeVore | |

FOREIGN PATENT DOCUMENTS

| | | | |
|---|---|---|---|
| CN | 203954068 U | 11/2014 | |
| EP | 0602965 A2 | 6/1994 | |
| FR | 2711120 A1 * | 4/1995 | ............ A61B 50/36 |
| JP | 06255682 A | 9/1994 | |
| JP | 2002282200 A | 10/2002 | |
| JP | 201029542 A | 2/2010 | |
| JP | 2010510517 A | 4/2010 | |
| JP | 201399395 A | 5/2013 | |
| WO | 2015174860 A1 | 11/2015 | |

OTHER PUBLICATIONS

Feyer, "Human factors in accident modelling," Encyclopedia of Occupational Heath and Safety, Fourth Edition, 1998.
First Office Action issued in Chinese Patent Application No. 201680048469.X mailed on Dec. 16, 2020, with English Translation.
Second Office Action issued in Chinese Patent Application No. 201680048469.X mailed on Apr. 27, 2020, with English Translation.
Notice of Reasons for Rejection issued in Japanese Patent Application No. 2018-509832, mailed Jul. 21, 2020, with English Translation.
Final Rejection issued in Japanese Patent Application No. 2018-509832, mailed Oct. 13, 2020, with English Translation.
Notice of Reasons for Rejection issued in Japanese Patent Application No. 2018-509832, mailed May 19, 2020, with English Translation.

* cited by examiner

SAFETY APPARATUS

CROSS-REFERENCE TO RELATED APPLICATIONS

This application is a Continuation of U.S. application Ser. No. 15/752,874, filed on Feb. 14, 2018, which is a national stage of International Application No. PCT/GB2016/052536, filed Aug. 16, 2016, which claims priority of United Kingdom Application No. 1514560.0, filed Aug. 16, 2015, and claims priority of United Kingdom Application No. 1522226.8, filed Dec. 16, 2015, and claims priority of United Kingdom Application No. 1522150.0, filed Dec. 15, 2015, the disclosures of which are incorporated by reference in their entireties.

FIELD OF THE INVENTION

The present invention relates generally to safety apparatus, and a method for its use, and in particular to safety apparatus for use in a medical procedure.

BACKGROUND

When humans perform complex tasks, or even simple tasks under pressure, mistakes can occur. The consequences of such mistakes are always undesirable, and sometimes catastrophic. It has been estimated that up to 90% of all workplace accidents have human error as a cause (Feyer, A. M. & Williamson, A. M. (1998): Human factors in accident modelling. In: Stellman, J. M. (Ed.), Encyclopaedia of Occupational Health and Safety, Fourth Edition. Geneva: International Labour Organisation). Some industries, notably healthcare, experience long-term, continuous exposure to human error. The costs in terms of human life and money are high (Institute of Medicine (2000): To err is human: Building a safer health system. Washington: National Academy Press). Placing emphasis on reducing human error may help reduce these costs.

In order to address human factors in workplace safety settings, capabilities and limitations must be understood and systems and procedures designed accordingly, remembering that the modern working environment is very different to the settings that humans have evolved to deal with. Such systems and procedures can mitigate risks and reduce the rate of occurrence of errors but not eliminate them completely. In certain situations, human beings will always make mistakes and there is a limit to what can be done to modify behaviour itself.

The most extreme instances of error in healthcare are the so-called "never events"; particularly shocking medical errors that should never occur which are unambiguous (clearly identifiable and measurable), serious (resulting in death or significant disability), and usually preventable if the available measures have been implemented by healthcare practitioners. Never events occur in many different areas of healthcare, including invasive procedures. In the National Health Service in England it is reported that never events relating to invasive procedures comprise 85% of all reported never events. Invasive procedure never events often involve the loss of or retention of medical apparatus in patients post-procedure (known as "retained instrument post operation").

An example of an invasive procedure never event is the retention of a guide wire after a catheter insertion procedure. Currently, guide wires are used to assist in the placement of percutaneous catheters in blood vessels or other body spaces. Examples of percutaneous catheters include central venous catheters, arterial catheters, chest drains, intra-aortic balloon pumps, thoracic catheters, tracheostomies and the like. Using a technique known as the Seldinger Technique, a needle or trocar is inserted into the structure and a guide wire is then passed through the needle. The needle is removed, a dilator may be passed and removed to open up the channel and then the catheter is passed over the guide wire into position. The guide wire should then be removed, and the catheter is commonly then stitched to the skin or attached by staples or adhesives or adhesive tapes or the like. Then a dressing is applied. The dressing may be impregnated or contain antiseptic agents. The never event occurs where the step of guide wire removal is omitted as a result of human error. As will be appreciated, the consequences for the patient of leaving the guide wire behind can be very severe and sometimes fatal.

SUMMARY OF THE INVENTION

Many invasive procedures require the performance of a set of actions by the clinician according to a sequence. It is an object of the present invention to provide apparatus and a method that utilises this in order to seek to mitigate problems such as those described above.

According to a first aspect of the invention there is provided safety apparatus for use in a procedure comprising at least first and second devices, wherein the first and second devices comprise devices for use in a medical procedure, the apparatus comprising a disabling mechanism that is adapted to releasably retain and thereby prevent use of the said second device until release by a release procedure using the first device. It is advantageous to provide a safety apparatus that requires a first device to release and make useable a second device. For example, a guide wire that has been used in a surgical procedure may be used as the first device to release apparatus for suturing and/or dressing a wound from the safety apparatus. This would ensure that a surgeon who has just performed a medical procedure must remove the guide wire from a patient in order to open the safety device and proceed to the final step of suturing and dressing a wound made during the procedure. Creating a second purpose for the guide wire ensures its removal from the patient and the safety apparatus therefore provides a set protocol that must be followed. This would limit medical mistakes such as leaving the guide wire inside a patient and closing the wound created during the medical procedure.

It is preferred that the first and second devices comprise devices for use in an invasive surgical procedure.

The disabling mechanism may be adapted to render the second said device inoperable until release by the first device. Alternatively, the disabling mechanism may be adapted to substantially enclose the second device to prevent its use. Making the second device inoperable or enclosed ensures that the first device must be available in order to render the second device useable.

It is preferred that the disabling mechanism is adapted to retain the first said device as part of the release procedure for the second said device. It is further preferred that the disabling mechanism is adapted such that release of the second device is only achieved upon and/or as a result of substantial enclosure of the first said device by the disabling mechanism. This has the advantage of placing procedural steps in place that must be followed in sequence during a procedure. The advantage of this is that it reduces or removes the possibility of human error by requiring that the first device is located and present in order to proceed with the next step of using the second device.

It is preferred that the disabling mechanism comprises a receptacle having an openable and closable lid, a first interior volume adapted to contain the second said device, and a lock mechanism for the lid that is only operable by use of the first said device.

It is further preferred that the receptacle comprises a second interior volume adapted to retain and substantially enclose the first said device when the lock mechanism has been actuated. It is further preferred that the shape of the interior volume substantially corresponds to the shape of the first said device. This is advantageous as it ensures that the safety device takes up no more space than is required to enclose the second device. If the second device is for use in a medical procedure, then this is very beneficial as space is at a premium in an operating theatre in which multiple instruments and devices are required.

It is preferred that the second interior volume forms a channel within the lid.

It is preferred that the channel has a first aperture for the first device to enter the second interior volume and a second aperture for the first device to exit the second interior volume. This is particularly advantageous when the first device is a wire, for example a guide wire, as it allows the wire to be threaded through the apertures such that the ends of the wire for a lever that can be used to pull open the openable and closable lid.

It is preferred that the second interior volume is loop or arch shaped.

It is preferred that the receptacle comprises a lower base surface, at least four side walls, and the lid to define the first interior volume, wherein the openable and closable lid has an open configuration and a closed configuration, wherein in the closed configuration the lid forms a substantially planar surface with the at least four side walls of the receptacle such as to prevent opening of the lid without the first device.

It is preferred that the locking mechanism comprises magnets. Using a magnet to seal the lid to the receptacle reduces complexity of the device which means that it is cheap and easy to manufacture. In addition, it is a robust system that is less likely to fail than a complex locking system.

It is preferred that the magnets are located on the lid.

It is preferred that the magnets are located on the lid and the lower base surface of the receptacle.

It is preferred that the first device is a guide wire.

It is preferred that the second device is apparatus for suturing and/or dressing a wound. This apparatus may include dressings, stitch or other suture devices, or adhesive.

It is preferred that the disabling mechanism includes means to indicate to a user that it has been used. The indicating means may comprise a transparent part. This is a simple and advantageous means to indicate that the first device is properly positioned and retained by the device after insertion.

According to a second aspect of the invention there is provided a method of carrying out a procedure comprising the use of at least first and second devices, the method comprising the steps of using the first device, applying the first device to a disabling mechanism to allow use of the second device, and using the second device.

It is preferred that the method comprises a medical procedure.

It is preferred that the method comprises an invasive surgical procedure.

It is preferred that the method comprises the step of rendering the first device incapable of reuse by the step of applying it to release the second device.

According to a third aspect of the invention there is provided a kit for carrying out a procedure comprising the safety device of the first aspect of the invention and the second device.

According to a fourth aspect of the invention there is provided a method of manufacturing the safety device according to the first aspect of the invention.

BRIEF DESCRIPTION OF THE DRAWINGS

The invention will further be described by way of example, with reference to the accompanying drawings in which.

DETAILED DESCRIPTION

Figure 1:
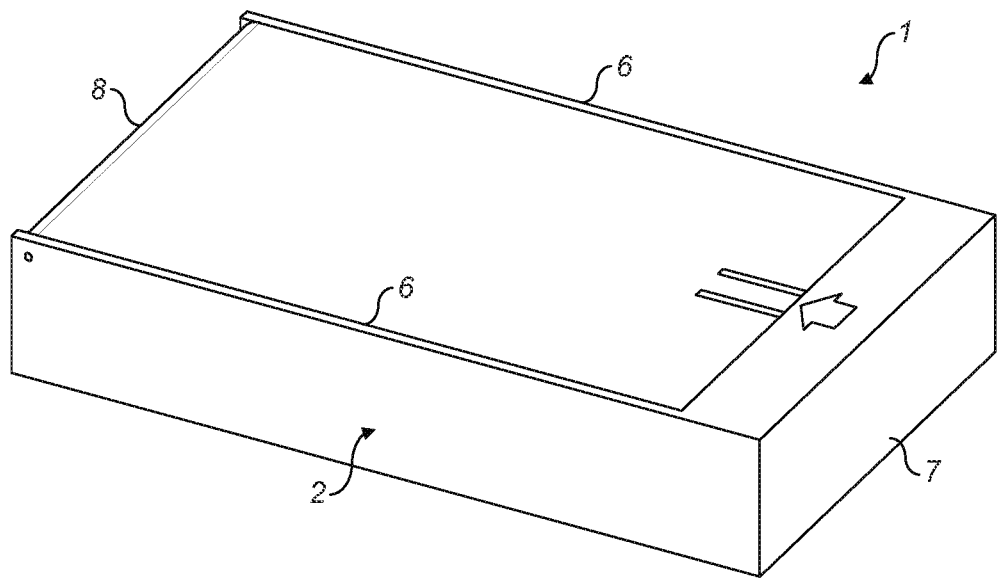
FIG. 1 is a perspective view of apparatus according to the invention.
Figure 2:
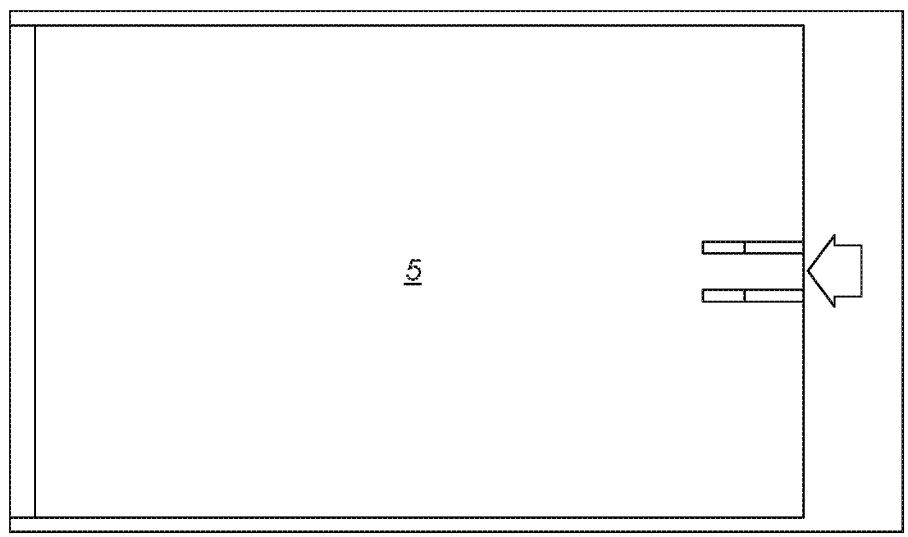
FIG. 2 is a plan view of the apparatus of FIG. 1.

Referring to the drawings there is illustrated safety apparatus 1, for use in a procedure comprising at least first and second devices, the apparatus comprising a disabling mechanism 2 that is adapted to releasably prevent use of the said second device until release therefrom by the first device.

In this example the apparatus 1 is intended for use in a Seldinger Technique catheter insertion procedure. Thus in this example the first device is a guide wire and the second device can be any or all of the devices used thereafter in the procedure, namely dressings, stitch or other suture devices, or adhesive.

Referring to FIG. 1, the disabling mechanism 2 takes the form of a rectangular box formed from an injection moulded plastics material. The box 2 includes integrally moulded base 3, sides 4 and front and back sides 7 and 8 that define an opening. A lid 5 completely closes the opening. As can be seen from FIG. 1, when the lid 5 is closed it fits flush with the top edges 6 of the sides 4 within the opening and with only a small gap therebetween. The lid is attached to the box by hinge pins (not shown).

Figure 3:
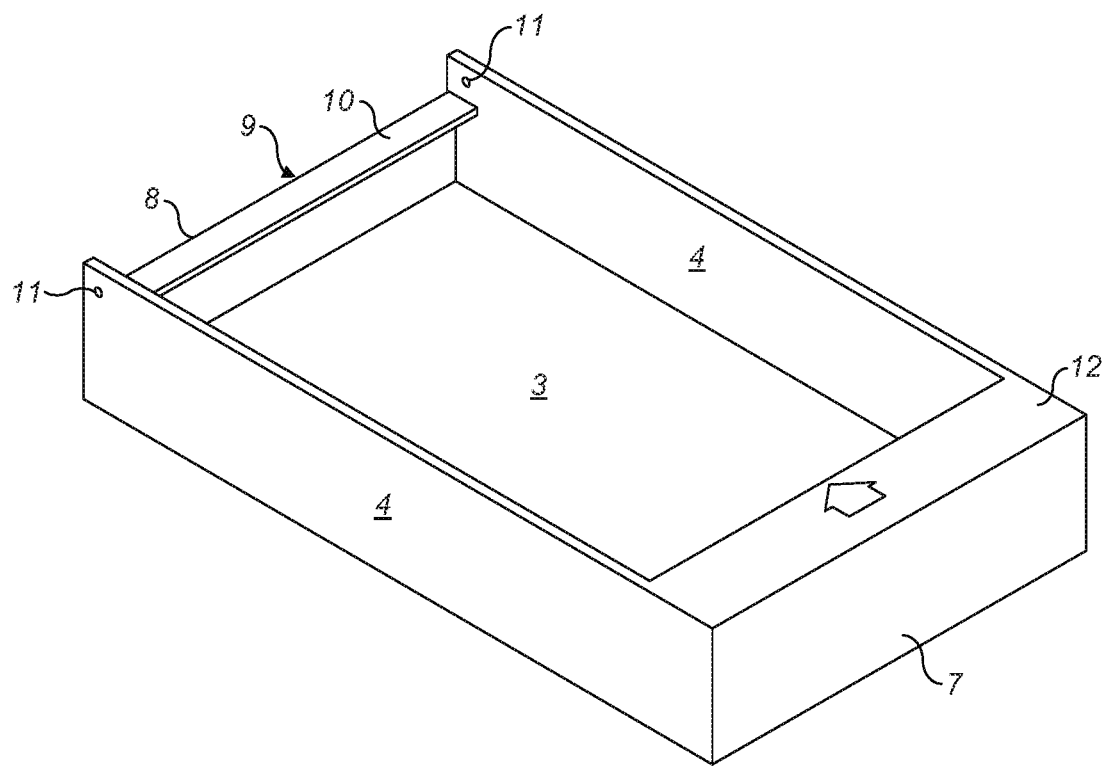
FIG. 3 is a perspective view of a base of the apparatus of FIG. 1.
Figure 6:
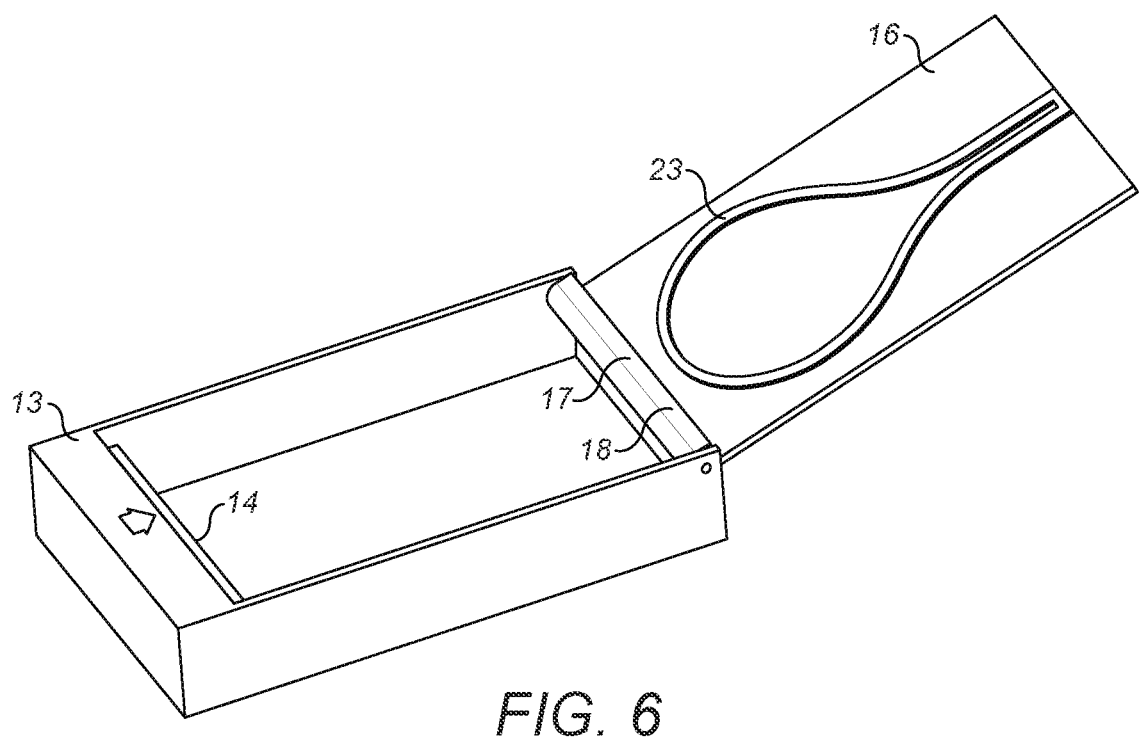
FIG. 6 is a perspective view of the apparatus of FIG. 1 in a first position.

FIGS. 3 and 6 show the interior volume of the box 2. The back side 8 is lower, relative to the other three sides 4, 7 and its top edge 9 includes a flange 10 that extends inwardly towards the interior volume. Sides 4 are provided with through holes 11 above flange 10. Front side 7 has substantially the same vertical extent as sides 4 but also includes a flange 12, but in this case the flange 12 includes a first flat land 13 in the same plane as the top edges 6 of the sides 4, and a second flat land 14 in the same plane as flange 10. In some embodiments, the flat land 14 may be a recessed shelf.

Figure 4:
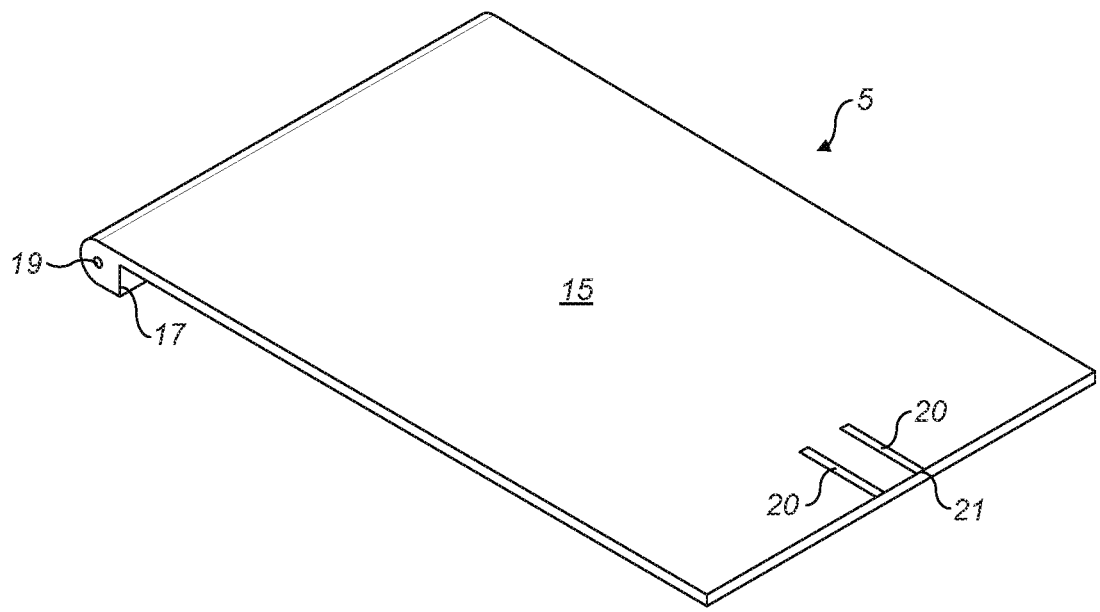
FIG. 4 is a perspective view of a lid of the apparatus of FIG. 1.
Figure 5:
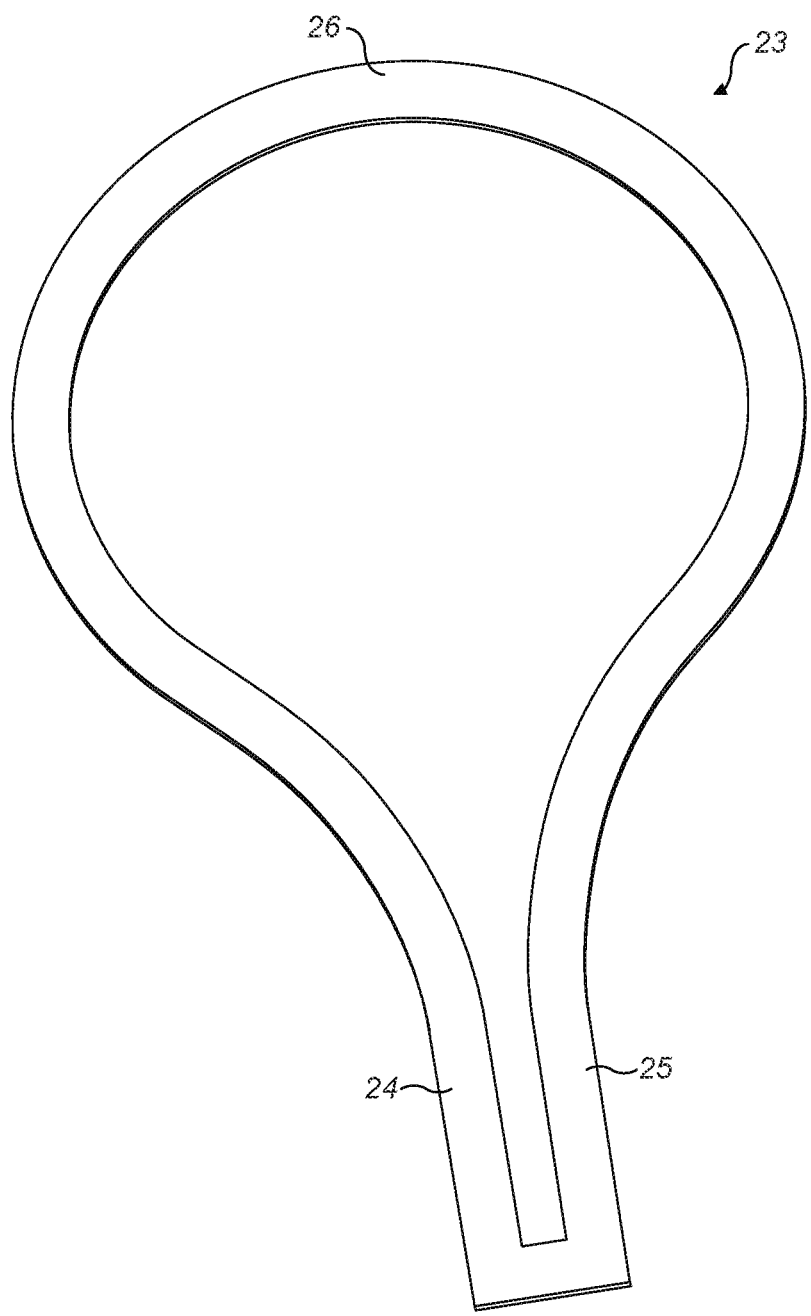
FIG. 5 is a perspective view of a part of the lid of the apparatus of FIG. 1.

FIGS. 4, 5 and 6 show details of the lid 5. The lid 5 comprises a substantially rectangular moulded plastics plate, including an upper surface 15, a lower surface 16 and a hinge formation 17. Hinge formation 17 comprises an elongate body 18 integrally formed at and extending downwardly (in use) from the lower surface 16 of the lid adjacent its back edge. The hinge formation 17 includes a blind bore 19 extending inwardly as viewed from each end (FIG. 4).

At its front edge the lid 5 is provided with two parallel channels 20 spaced equally from and parallel to a longitudinally extending central axis. The channels 20 extend about one tenth of the longitudinal extent of the lid. Each channel 20 includes a floor 21 that slopes downwardly, as viewed, at angle of about 30 degrees from the level of the upper surface 15 of the lid towards apertures 22 that open out through the lower surface 16.

Figure 8:
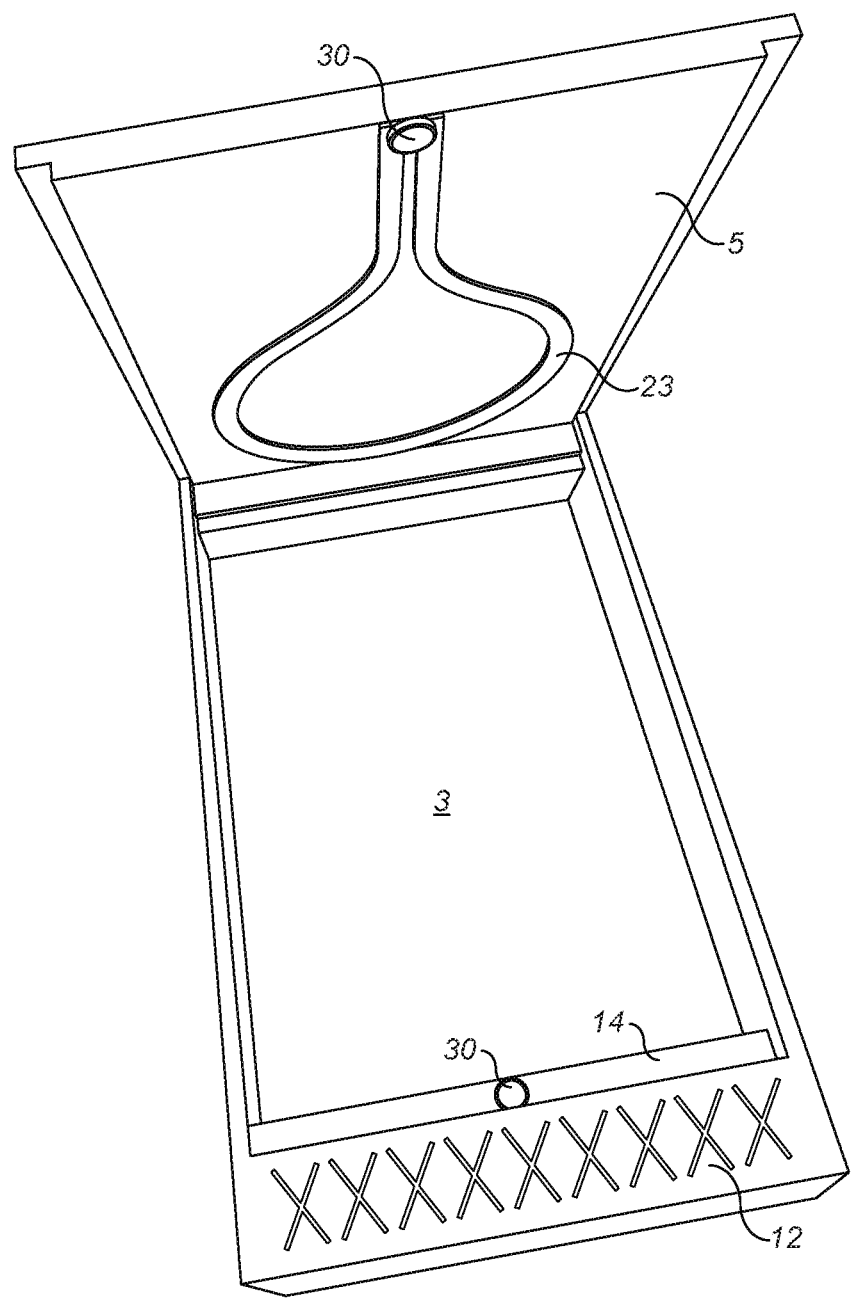
FIG. 8 is a perspective view of a second embodiment of apparatus according to the invention.

A guide wire retaining channel 23 is located on the lower surface 16 of the lid 5. In this embodiment the guide wire retaining channel 23 comprises an elongate moulded plastics tube which includes first and second linear sections 24, 25 connected by a curved section 26. The tube includes a through bore 27 that extends its entire length and is dimensioned to accommodate a guide wire. The tube is attached to the lower surface 16 of the lid so that each end of the through bore 27 is in register with an aperture 22 of the channels 20. The through bore 27 is configured to be a few centimetres shorter than the length of the guide wire with which it is intended to be used. As will be appreciated, different configurations of guide wire retaining channel 23 can be provided, for example, by forming an open channel in the lower surface of the lid and covering it with a simple flat cover (FIG. 8).

The guide wire retaining channel 23 must be large enough to accommodate all sizes and gauges of guide wires which may be used, allowing for ease of passage of the guide wire.

Figure 7:
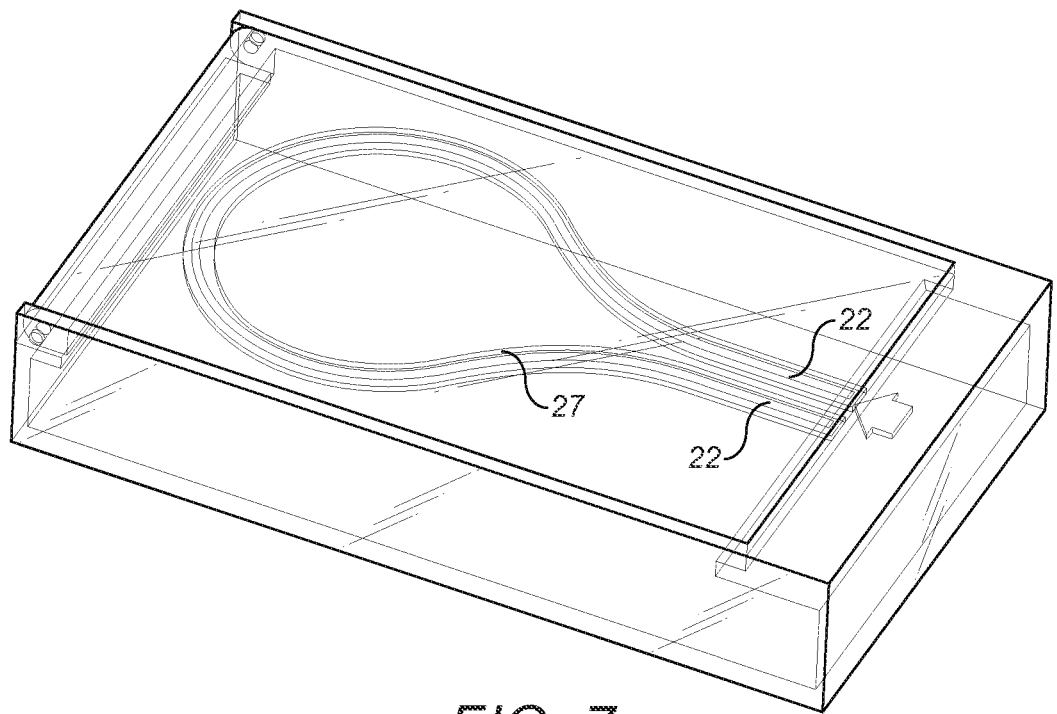
FIG. 7 is a perspective view of the apparatus of FIG. 1 in a second position.

As can be seen from FIGS. 6 and 7, when the lid 5 is in the closed position its front and rear edges are supported upon flange 10 and land 14 so that the lid cannot fall into the box. The lid 5 can be made to be a simple interference fit with the sides, back and front 4, 7, 8 when it is in the closed position, or alternatively a latch mechanism can be provided. In a second embodiment, the lid may be secured in the closed position using magnets. In this embodiment (shown in FIG. 8), a magnet 30 is provided on both the front lower lid 5 and the recessed shelf or land 14 to hold the recessed lid in the closed position.

In use, the box 2 is provided to a user including dressings, stitch or other suture devices, or adhesive. The lid 5 is closed and cannot easily be opened because of frictional forces. After use of a guide wire, the user must insert the guide wire into the guide wire retaining channel 23 by feeding it into one of the channels 20 so that it passes around the curved section 26 and reappears from the other channel 20. The guide wire itself can then be used to apply upward pressure to the lid to open it and gain access to the contents.

From the above description it will appreciated that in this embodiment the invention provides a box or container or packaging that is locked closed and requires the wire to be placed in the proximity of, placed on or inserted into a hole in the box which unlocks the box and allows the clinician access to the contents. The description of catheter placement as described above, indicates that a clinician who has forgotten to remove the wire, would normally proceed to stitch or otherwise secure the wire to the patient's skin and place a sterile dressing over the insertion site. Using the current invention, the dressing and/or the stitch or other suture devices, or adhesives required to complete the procedure could only be accessed if the clinician uses the guide wire to open the container. This means the guide wire must have been removed.

One alternative embodiment of the invention has a hole in which the end of the wire is threaded which manually pushes and unlocks a locking mechanism.

A further embodiment of the invention has a slot that the side of the wire can be slotted into to manually push elements which will unlock the container.

A further embodiment of the invention has a pathway for a wire which encircles or partially encircles the container and an encircling or partially encircling wire can be pulled tight by both ends to enable friction to pull open the locking mechanism.

A further embodiment of the invention is a packaging for a stitch or other suture devices that is difficult to open unless a wire is placed through a hole thereby enabling the package to be easily ripped open.

A further embodiment of the invention has an opening mechanism that traps the guide wire so that it cannot be removed thereby preventing the clinician from using the guide wire prior to catheter placement to open the invention.

A further embodiment of the invention can be sterilised to enable it to be used within a sterile field.

Figure 9:
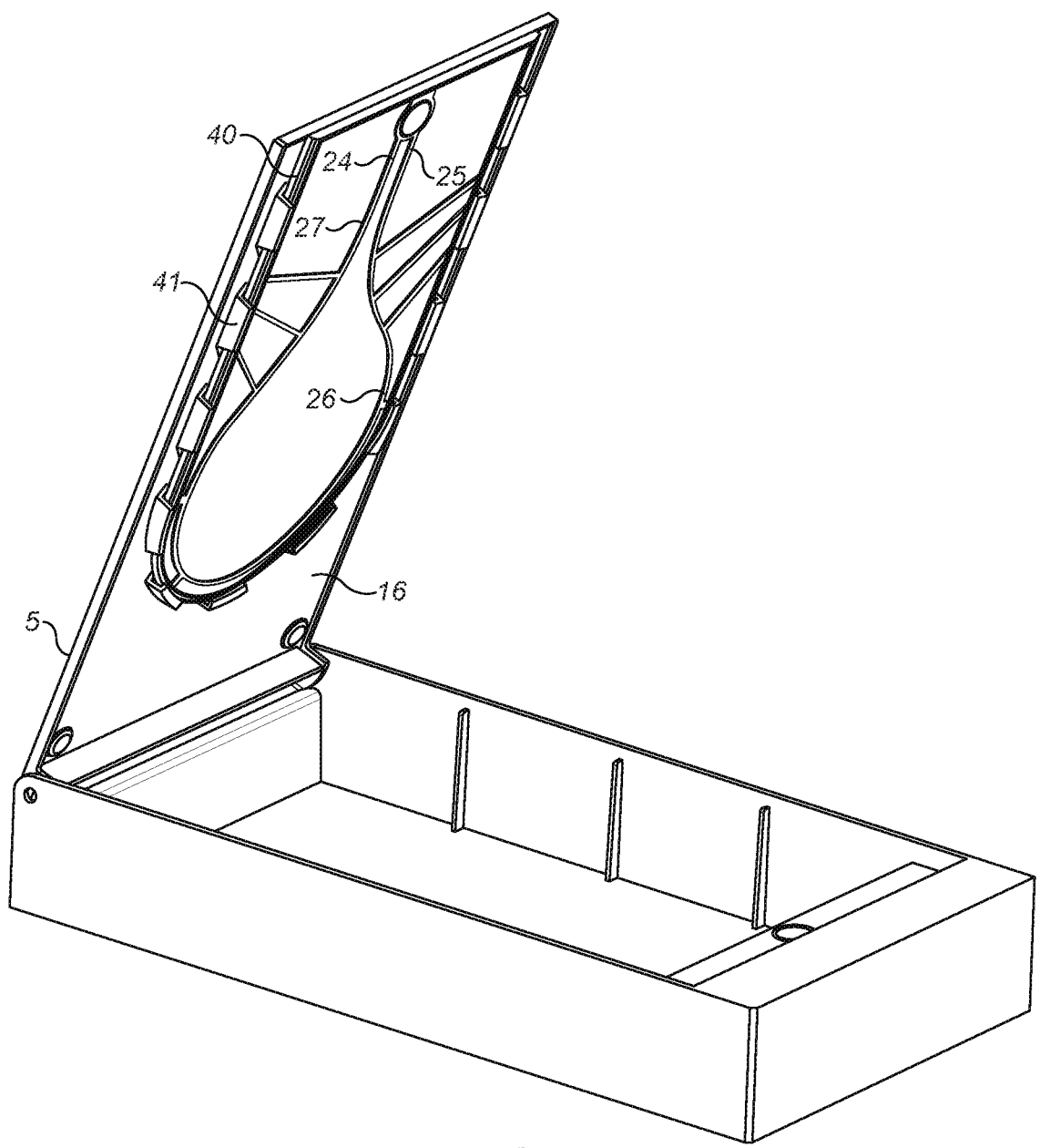
FIG. 9 is a perspective view of a third embodiment of apparatus according to the invention.

In a further embodiment shown in FIG. 9, the guide wire retaining channel 23 is located in a separate component affixed to the lower surface 16 of the lid 5. In this embodiment, the guide wire retaining channel 23 comprises a separate plate 40 which slots into hooks 41. The guide wire retaining channel comprises a channel which includes first and second linear sections 24, 25 connected by a curved section 26. The tube includes a through bore 27 that extends its entire length and is dimensioned to accommodate a guide wire. The through bore 27 is in register with an aperture 22 of the channels 20 (not shown) on the upper surface of the lid 5 such that the guide wire may be inserted through the channels 20 (not shown) on the upper surface of the lid 5 and into the guide wire retaining channel 23 in the plate 40.

In order to test the efficacy of this approach an experiment was performed as follows:

Materials and Methods: A Safety Procedure Pack (SPP) was prepared consisting of a box 2 containing the stitch, stitch holder and anti microbial dressing required to complete the procedure. The SPP had a recessed lid which could only be opened by inserting a guidewire into a hole labelled "insert guidewire here". With IRB approval and written consent, doctors experienced in independent CVC placement were randomised to routine practice (RP) or SPP groups. All were presented with a scenario whereby a colleague who was mid-CVC insertion had been called away to an emergency. Participants were asked to safely complete the procedure. The manikin model had the CVC inserted with the guide wire left intra-luminally in the distal lumen, visible through the transparent tubing to the hub and retrievable with forceps from the hub. No guidewire was present on the trolley or in the otherwise empty sharps bin. A cardio monitor showed ectopic beats. If specifically asked, the only information that the junior assistant knew was that the SPP was a new safety procedure pack recently introduced into the hospital containing the sutures and dressings which could be used as a sharps repository after placement.

Results and Discussion: The SPP completely prevented guidewire retention (80% RP v 0% SPP retention, n=20, $p<0.001$ by Fishers Exact test). In the control RP group 8 completed simulation of suturing, dressing and returning the patient to the ward with the guidewire left in place. In the SPP group participants underwent searches of combinations of trolley, floor, sharps bin and domestic bin before the realisation of the intra-luminal location of the wire. All wires were eventually removed without complications. A structured questionnaire for the SPP group examined feedback for their first use of the SPP. All participants indicated the SPP improved practice in terms of guidewire safety, convenience and sharps/wire disposal safety.

Conclusions: The SPP was 100% successful in preventing the never event of CVC guidewire retention alongside facilitating normal insertion.

The invention claimed is:

1. A safety apparatus for use in a medical procedure, the safety apparatus comprising:
    at least first and second devices for use in an invasive surgical procedure, and
    further comprising a disabling mechanism releasably retaining and thereby preventing use of the second device until release by a release procedure using the first device,
    wherein the first device is a guide wire.
2. The safety apparatus according to claim 1, wherein the disabling mechanism is adapted to render the second device inoperable until release by the first device.
3. The safety apparatus according to claim 1, wherein the disabling mechanism is adapted to substantially enclose the second device to prevent its use.
4. The safety apparatus according to claim 1, wherein the disabling mechanism is adapted to retain the first device as part of the release procedure for the second device.
5. The safety apparatus according to claim 1, wherein the disabling mechanism is adapted such that release of the second device is only achieved upon and/or as a result of substantial enclosure of the first device by the disabling mechanism.
6. The safety apparatus according to claim 1, wherein the disabling mechanism comprises a receptacle having an openable and closable lid, a first interior volume adapted to contain the second device, and a lock mechanism for the lid that is operable by use of the first device.
7. The safety apparatus according to claim 6, wherein the disabling mechanism comprises a second interior volume adapted to retain and substantially enclose the first device when the lock mechanism has been actuated.
8. The safety apparatus according to claim 7, wherein the shape of the second interior volume substantially corresponds to the shape of the first device.
9. The safety apparatus according to claim 7, wherein the second interior volume forms a channel within the lid.
10. The safety apparatus according to claim 9, wherein the channel has a first aperture for the first device to enter the second interior volume and a second aperture for the first device to exit the second interior volume.
11. The safety apparatus according to claim 7, wherein the second interior volume is loop or arch shaped.
12. The safety apparatus according to claim 6, wherein the receptacle comprises a lower base surface, at least four side walls, and the lid to define the first interior volume, wherein the openable and closable lid has an open configuration and a closed configuration, wherein the closed configuration the lid forms a substantially planar surface to the top of the at least four side walls of the receptacle such as to prevent opening of the lid without the first device.
13. The safety apparatus according to claim 12, wherein magnets are located on the lid and the lower base surface of the receptacle.
14. The safety apparatus according to claim 6, wherein the lock mechanism comprises magnets.
15. The safety apparatus according to claim 14, wherein the magnets are located on the lid.
16. The safety apparatus according to claim 1, wherein the disabling mechanism includes indicating means to a user that it has been used.
17. The safety apparatus according to claim 16, wherein the indicating means comprises a transparent part.
18. The safety apparatus according to claim 1, wherein the second device is means for suturing and/or dressing a wound.
19. A kit for carrying out a procedure, comprising the safety apparatus of claim 1, wherein the procedure includes the medical procedure for which the safety apparatus is used, the kit including the first device and the second device.
20. The safety apparatus according to claim 1, wherein the disabling mechanism comprises a channel dimensioned to accommodate the first device.
21. A safety apparatus for use in a medical procedure, the safety apparatus comprising:
    at least first and second devices for use in an invasive surgical procedure, and
    further comprising a disabling mechanism releasably retaining and thereby preventing use of the second device until release by a release procedure using the first device,
    wherein the second device is means for suturing and/or dressing a wound.
22. The safety apparatus according to claim 21, wherein the disabling mechanism is adapted to render the second device inoperable until release by the first device.
23. The safety apparatus according to claim 21, wherein the disabling mechanism is adapted to substantially enclose the second device to prevent its use.
24. The safety apparatus according to claim 21, wherein the disabling mechanism is adapted to retain the first device as part of the release procedure for the second device.
25. The safety apparatus according to claim 21, wherein the disabling mechanism is adapted such that release of the second device is only achieved upon and/or as a result of substantial enclosure of the first device by the disabling mechanism.
26. The safety apparatus according to claim 21, wherein the disabling mechanism comprises a receptacle having an openable and closable lid, a first interior volume adapted to contain the second device, and a lock mechanism for the lid that is operable by use of the first device.
27. The safety apparatus according to claim 26, wherein the disabling mechanism comprises a second interior volume adapted to retain and substantially enclose the first device when the lock mechanism has been actuated.
28. The safety apparatus according to claim 27, wherein the shape of the second interior volume substantially corresponds to the shape of the first device.
29. The safety apparatus according to claim 27, wherein the second interior volume forms a channel within the lid.
30. The safety apparatus according to claim 29, wherein the channel has a first aperture for the first device to enter the second interior volume and a second aperture for the first device to exit the second interior volume.
31. The safety apparatus according to claim 27, wherein the second interior volume is loop or arch shaped.
32. The safety apparatus according to claim 26, wherein the receptacle comprises a lower base surface, at least four side walls, and the lid to define the first interior volume, wherein the openable and closable lid has an open configuration and a closed configuration, wherein the closed configuration the lid forms a substantially planar surface to the top of the at least four side walls of the receptacle such as to prevent opening of the lid without the first device.

33. The safety apparatus according to claim 32, wherein magnets are located on the lid and the lower base surface of the receptacle.

34. The safety apparatus according to claim 26, wherein the lock mechanism comprises magnets.

35. The safety apparatus according to claim 34, wherein the magnets are located on the lid.

36. The safety apparatus according to claim 21, wherein the disabling mechanism includes indicating means to a user that it has been used.

37. The safety apparatus according to claim 36, wherein the indicating means comprises a transparent part.

38. A kit for carrying out a procedure, comprising the safety apparatus of claim 21, wherein the procedure includes the medical procedure for which the safety apparatus is used, the kit including the first device and the second device.

39. The safety apparatus according to claim 21, wherein the disabling mechanism comprises a channel dimensioned to accommodate the first device.

\* \* \* \* \*